(12) United States Patent
Fagan

(10) Patent No.: US 12,201,530 B2
(45) Date of Patent: Jan. 21, 2025

(54) LUMBAR VERTEBRAE FUSION DEVICE WITH INTERNAL EXTENSION MECHANISM

(71) Applicant: Orthopedic Designs North America, Inc., Tampa, FL (US)

(72) Inventor: Lance Fagan, Tampa, FL (US)

(*) Notice: Subject to any disclaimer, the term of this patent is extended or adjusted under 35 U.S.C. 154(b) by 348 days.

(21) Appl. No.: 17/822,147

(22) Filed: Aug. 25, 2022

(65) Prior Publication Data
US 2024/0065852 A1     Feb. 29, 2024

(51) Int. Cl.
*A61F 2/44* (2006.01)
*A61B 17/70* (2006.01)

(52) U.S. Cl.
CPC ........ *A61F 2/4455* (2013.01); *A61B 17/7011* (2013.01)

(58) Field of Classification Search
CPC ............................... A61F 2/4455; A61F 2/447
See application file for complete search history.

(56) References Cited

U.S. PATENT DOCUMENTS

| | | | |
|---|---|---|---|
| 6,447,546 B1 * | 9/2002 | Bramlet | A61F 2/446 623/17.11 |
| 8,968,405 B2 * | 3/2015 | Kirwan | A61F 2/447 623/17.11 |
| 9,445,913 B2 * | 9/2016 | Donner | A61B 17/846 |
| 9,517,144 B2 * | 12/2016 | McAtamney | A61F 2/30749 |
| 9,566,165 B2 * | 2/2017 | Lee | A61F 2/30749 |
| 9,693,876 B1 * | 7/2017 | Mesiwala | A61F 2/4455 |
| 9,717,600 B1 * | 8/2017 | Wensel | A61B 17/70 |
| 9,877,842 B2 * | 1/2018 | Chataigner | A61F 2/4611 |
| 9,937,050 B2 * | 4/2018 | Dinville | A61F 2/4455 |
| 10,137,005 B2 * | 11/2018 | Ashleigh | A61F 2/4611 |
| 10,398,565 B2 * | 9/2019 | Bender | A61F 2/4455 |
| 10,433,975 B2 * | 10/2019 | Ashleigh | A61F 2/4455 |
| 10,433,980 B2 * | 10/2019 | Ashleigh | A61F 2/4611 |
| 10,765,531 B2 * | 9/2020 | Kim | A61F 2/4611 |
| 11,253,373 B2 | 2/2022 | Bender | |
| 11,432,944 B2 * | 9/2022 | Bernard | A61F 2/4455 |
| 11,491,025 B2 * | 11/2022 | Gilbride | A61F 2/447 |
| 11,529,241 B2 * | 12/2022 | Gamache | A61F 2/4611 |
| 2020/0383797 A1 | 12/2020 | Predick | |

\* cited by examiner

*Primary Examiner* — Ellen C Hammond
(74) *Attorney, Agent, or Firm* — Larson & Larson; Justin P. Miller; Frank Liebenow

(57) ABSTRACT

The spinal stabilization device is implanted using a surgical procedure referred to as an anterior lumbar interbody fusion (AILF). The body of the device includes upper and lower surfaces that are placed in direct contact with the adjacent vertebrae. After placement of the device between the vertebrae, a threaded member is rotated to cause the anchoring element to push into the body of the device, causing the extension of tangs through the upper and lower surfaces and into the adjacent vertebrae of the patient. Movement of the anchoring element with respect to the body is caused by rotation of a threaded actuator. The threaded actuator is a permanent element of the spinal stabilization device, rather than being integrated into a temporary tool.

12 Claims, 8 Drawing Sheets

LUMBAR VERTEBRAE FUSION DEVICE WITH INTERNAL EXTENSION MECHANISM

FIELD

This invention relates to the field of spinal fusion and more particularly to a device to bridge two vertebrae.

BACKGROUND

Fusion of spinal vertebrae is recommended to compensate for spinal degradation. Fusion prevents two vertebrae from moving with respect to each other, and is thus a means of addressing pain associated with motion. Potential locations for use of spinal fusion include the lumbar portion of the spine.

As part of spinal fusion, the degenerated disc is removed and replaced with a stabilizing device.

The vertebrae above and below the removed disc then fuse through device via bone growth.

During the period between installation of the device, and eventual fusion, there is a risk the stabilizing device will dislodge.

What is needed is a stabilizing device to affix a pair of adjacent vertebrae, the device securely fixed in place while bone is permitted to grow.

SUMMARY

The spinal stabilization device is implanted using a surgical procedure referred to as an anterior lumbar interbody fusion (AILF).

An AILF Surgery is performed through the front of the body, the device placed into the spine.

To make room for the device the intervertebral disc is removed and replaced with the lumbar vertebrae fusion device with internal expansion mechanism.

The lumbar vertebrae fusion device with internal expansion mechanism includes one or more recesses into which the surgeon can place bone graft material. The bone graft material encourages the growth of the patient's bone through the device, affixing the device in place with respect to the spine.

The body of the device includes upper and lower surfaces that are placed in direct contact with the adjacent vertebrae. After placement of the device between the vertebrae, a threaded member is rotated to cause the anchoring element to push into the body of the device, in turn causing the extension of tangs through the upper and lower surfaces and into the adjacent vertebrae of the patient.

Movement of the anchoring element with respect to the body is caused by rotation of a threaded actuator. The threaded actuator is a permanent element of the spinal stabilization device, rather than being integrated into a temporary tool.

The integration of the actuator into the device itself is particularly beneficial if the device needs to be removed from the patient. Prior art devices integrate the actuating element into a temporary tool, meaning that when the surgeon needs to remove the tangs, it is the temporary tool that creates a force with respect to device, resulting in a force toward or away from the patient's spine.

In contrast, in the disclosed device the actuator is built-in, thus all that is required to cause retraction of the tangs is rotation of the head of the threaded element. Any torque that is created by this rotation is counteracted by the temporary tool held by the surgeon.

Stated differently, the prior art devices require the surgeon to brace a removable tool against the body of the device, pushing or pulling the anchor mechanism with respect to the tool. This creates a force toward or away from the user's spine. In contrast, the disclosed device is internally braced, with rotation of the threaded element causing the motion of the anchoring element with respect to the body of the device. Thus, the toward and away forces are limited to the device itself, the forces canceling out, thus avoiding any in or out force with respect to the user's spine.

Rotation of the threaded actuator to cause motion of the anchoring element with respect to the body can be accomplished in one of multiple ways. For example, by using different threads on the part of the threaded actuator that interacts with the anchoring element as compared to the portion of the threaded actuator that interacts with the body.

By using different threads, the amount of linear movement for the first set of threads and second set of threads is different. Threads may differ in pitch or in lead arrangement.

Regarding pitch, pitch is the distance from the crest of one thread to the next. A larger thread pitch means a greater length between threads, thus more linear movement for a single rotation.

Threads have a handedness, or direction of linear motion associated with rotation. Viewed from above, a right-handed thread will move away when rotated clockwise, and toward when rotated counterclockwise. A left-handed thread is the opposite, moving away when rotated counterclockwise and toward when rotated clockwise.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1A:
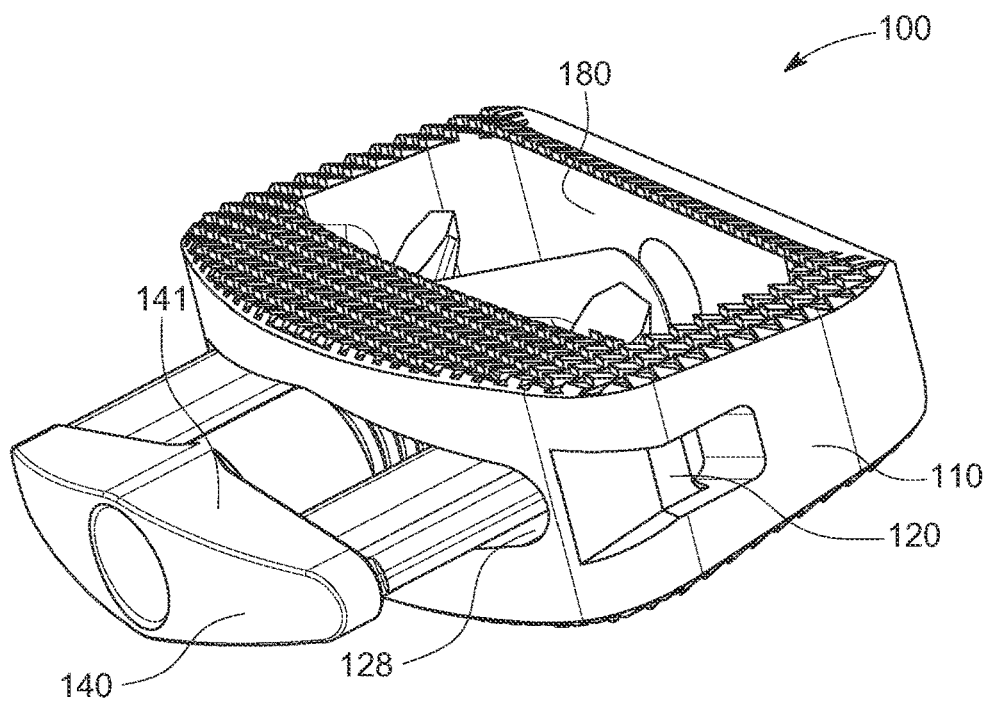
FIG. 1A illustrates a first isometric view of the lumbar vertebrae fusion device with internal extension mechanism in a retracted position.

Reference will now be made in detail to the presently preferred embodiments of the invention, examples of which are illustrated in the accompanying drawings. Throughout the following detailed description, the same reference numerals refer to the same elements in all figures.

Figure 1B:
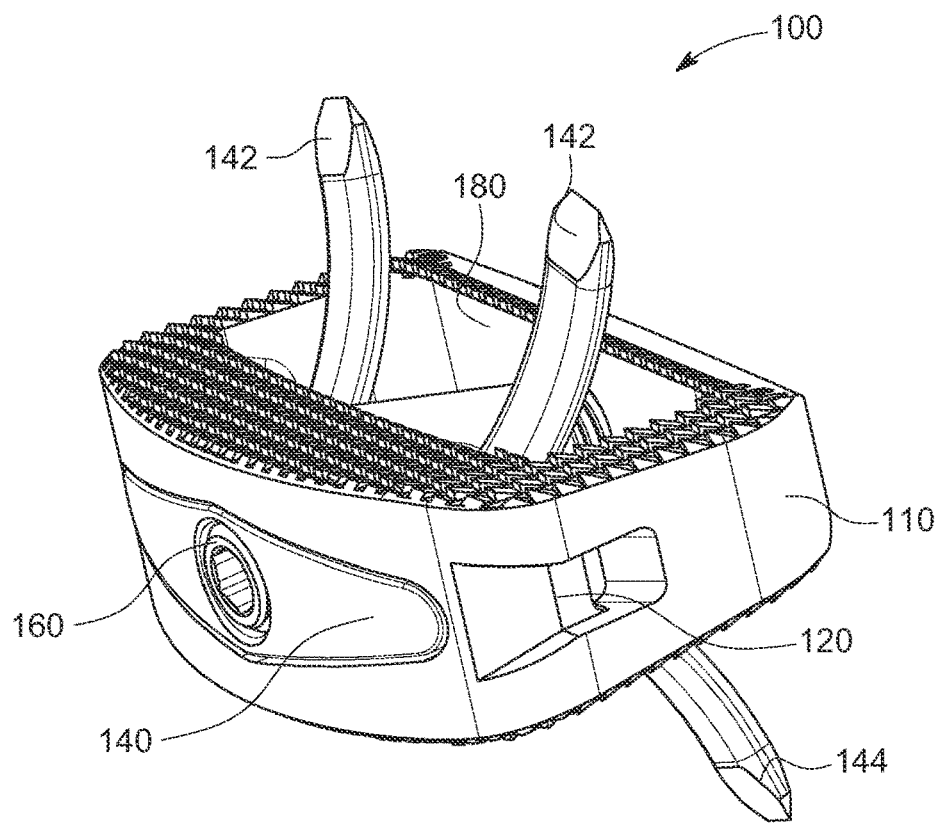
FIG. 1B illustrates a first isometric view of the lumbar vertebrae fusion device with internal extension mechanism in an extended position.

Referring to FIGS. 1A and 1B, a first isometric view of the lumbar vertebrae fusion device with internal extension mechanism in a retracted position and a first isometric view an extended position are shown.

The spinal stabilization device 100 is shown with body 110, the body 110 including tool interface recesses 120 into which the surgeon's insertion tool (not shown) fits to grip the spinal stabilization device 100.

The anchoring element 140 moves inwardly and outwardly with respect to the body 110, inward and outward movement caused by rotation of threaded actuator 160.

Inward movement of the anchoring element 140 causes extension of the upper tangs 142 and lower tangs 144, which then protrude beyond the body 110.

In its fully seated position, the anchoring element head 141 sits within the recess 128.

Also shown is cavity for bone graft 180.

Figure 2A:
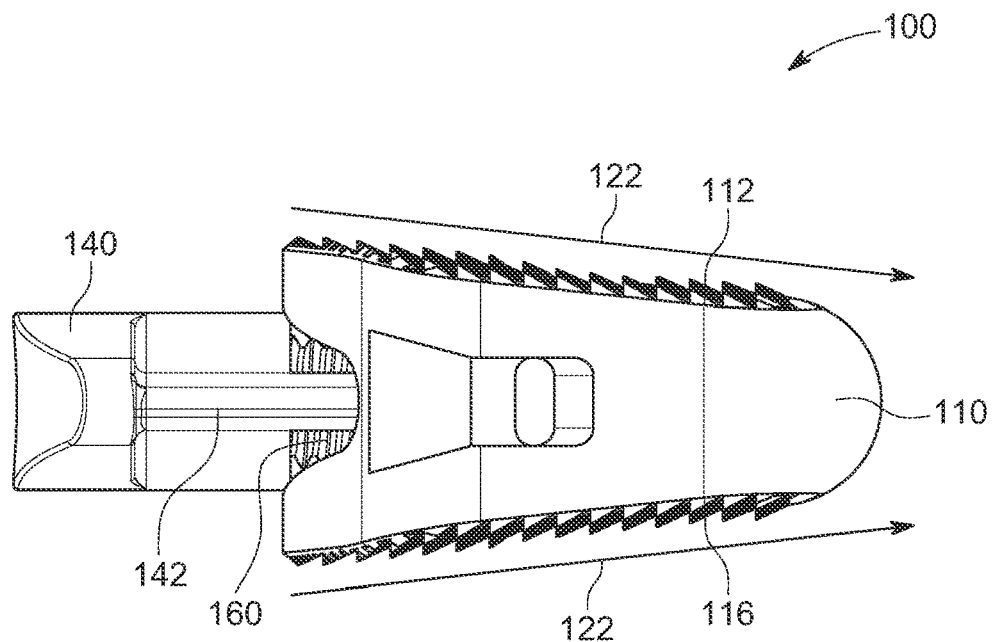
FIG. 2A illustrates a side view of the lumbar vertebrae fusion device with internal extension mechanism in a retracted position.
Figure 2B:
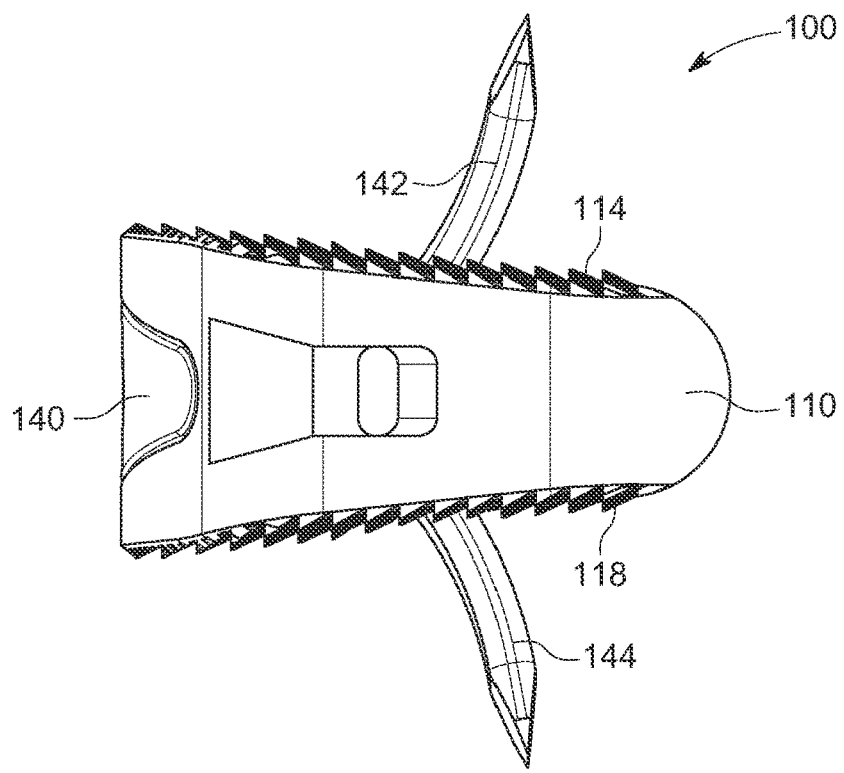
FIG. 2B illustrates a side view of the lumbar vertebrae fusion device with internal extension mechanism in an extended position.

Referring to FIGS. 2A and 2B, a side view of the lumbar vertebrae fusion device with internal extension mechanism in a retracted position and a side view in an extended position are shown.

In the preferred embodiment, the upper surface 112 and lower surface 116 of the body 110 are angled with respect to each other to create a tapered profile 122 that matches the preferred spacing between adjacent vertebrae. In other embodiments, the upper surface 112 and lower surface 116 have other shapes or angles with respect to each other to best conform to the adjacent vertebrae based upon the location of placement within the spine.

The upper surface 112 includes upper surface prongs 114 to discourage motion of the body 110 with respect to the vertebrae. Similarly, the lower surface 116 includes lower surface prongs 118.

The anchoring element 140 is moved by the threaded actuator 160 causing motion and deformation of the upper tangs 142 and lower tangs 144.

Figure 3A:
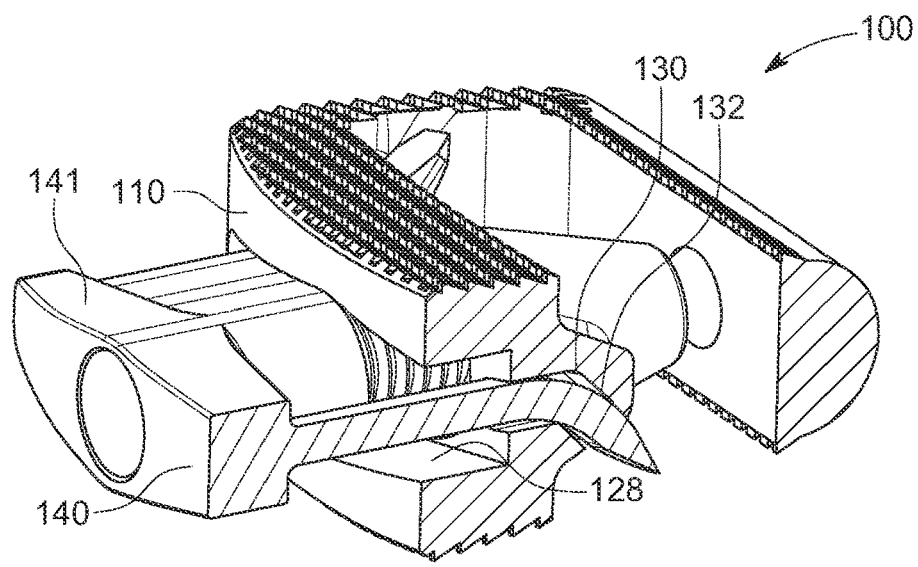
FIG. 3A illustrates a partial cross-sectional view of the lumbar vertebrae fusion device with internal extension mechanism in a retracted position.
Figure 3B:
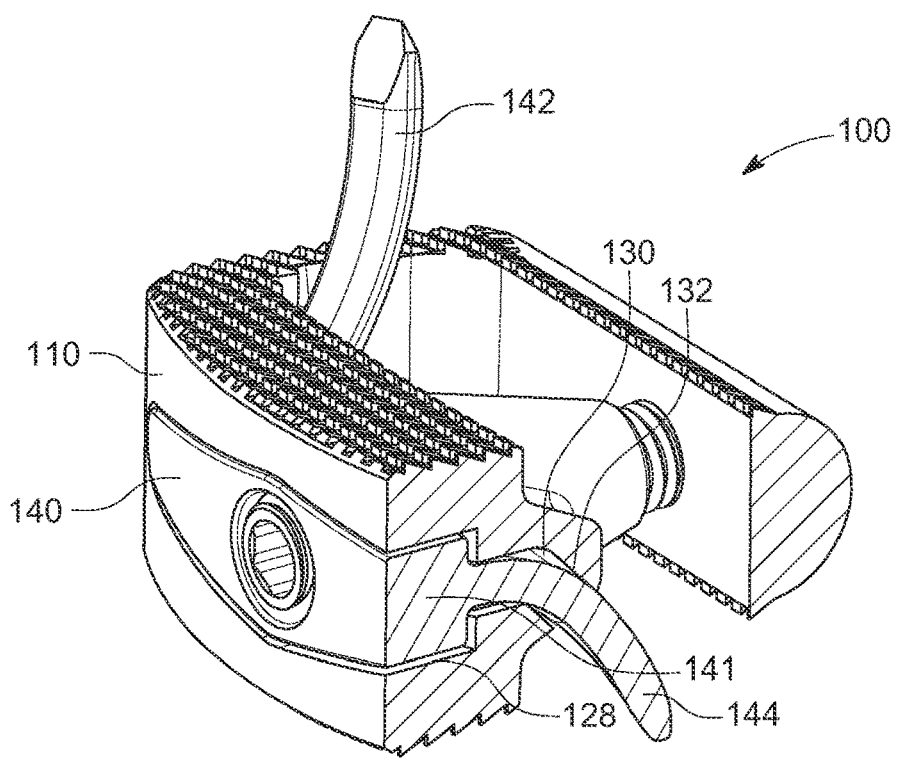
FIG. 3B illustrates a partial cross-sectional view of the lumbar vertebrae fusion device with internal extension mechanism in an extended position.

Referring to FIGS. 3A and 3B, a partial cross-sectional view of the lumbar vertebrae fusion device with internal extension mechanism in a retracted position and a partial cross-sectional view in an extended position are shown.

Motion of the lower tang 144 through the body 110, specifically through the tank deflection passage 130 with downward deflection ramp 132, is shown.

As the anchoring element 140, with head 141, moves toward the recess 128, the tangs 142/144 are forced through their respective tang deflection passages 130, the tangs causing plastic deformation of the tangs 142/144 as they change shape to protrude upward and downward beyond the body 110.

Figure 4A:
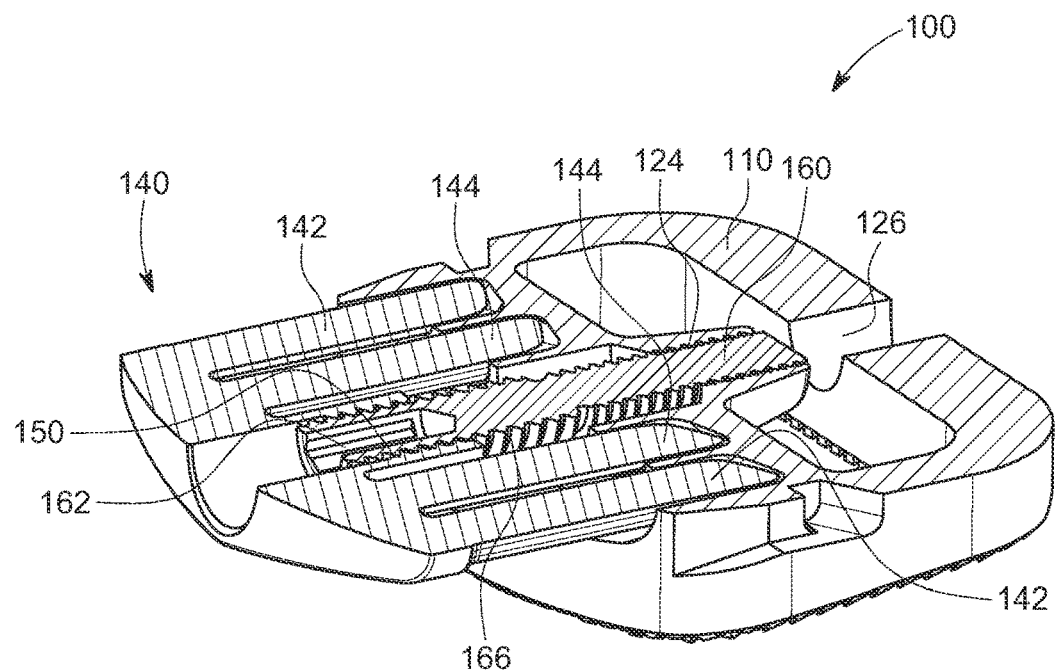
FIG. 4A illustrates a second partial cross-sectional view of the lumbar vertebrae fusion device with internal extension mechanism in a retracted position.
Figure 4B:
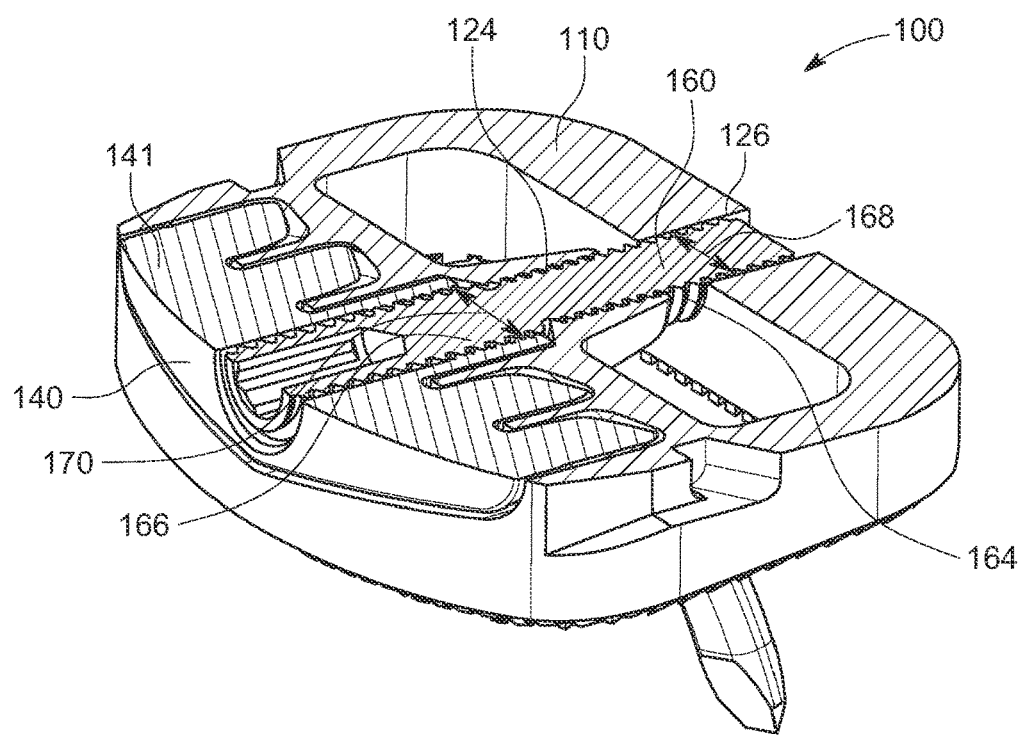
FIG. 4B illustrates a second partial cross-sectional view of the lumbar vertebrae fusion device with internal extension mechanism in an extended position.

Referring to FIGS. 4A and 4B, a second partial cross-sectional view of the lumbar vertebrae fusion device with internal extension mechanism in a retracted position and a second partial cross-sectional view in an extended position are shown.

The anchoring element 140 is moved by rotation of the threaded actuator 160. Threaded actuator 160 is interfaced with by the tool interface head 162, into which the surgeon inserts the actuator driver (not shown).

The threaded actuator 160 includes a first thread set 164 with first diameter 168 and a second thread set 166 with second diameter 170.

Body 110 includes a threaded actuator pass through 126, into which the threaded actuator 160 moves as the anchoring element 140 is pulled into the body 110.

The first thread set 164 interfaces with the first threaded actuator interface 124 of the body 110.

The second thread set 166 interfaces with the second threaded actuator interface 150 of the anchoring element 140.

As the threaded actuator 160 is rotated, the anchoring element 140 is drawn into the body 110. In the preferred embodiment, motion of the anchoring element with respect to the body is created by the first thread set 164 being of opposite pitch as compared to the second thread set 166. Stated differently, the first thread set 164 is, for example, right hand thread, and the second thread set 166 is, for example, left hand thread.

In an alternative embodiment both thread sets 164/166 shared the same thread direction, for example left hand thread, but have differing pitches resulting in a differing amount of linear motion per single rotation.

Figure 5A:
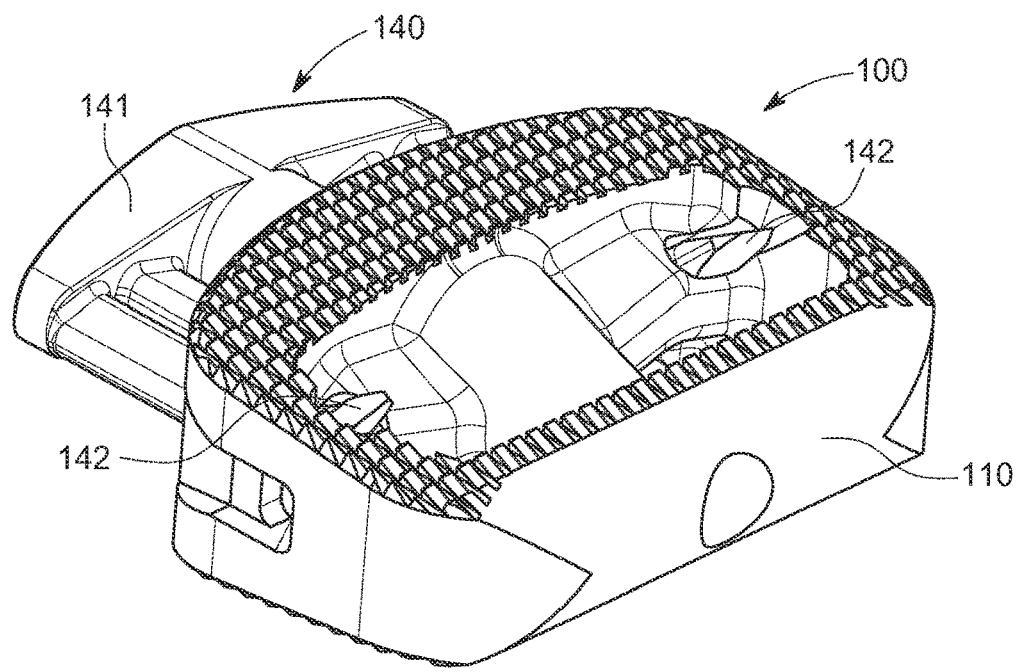
FIG. 5A illustrates a second isometric view of the lumbar vertebrae fusion device with internal extension mechanism in a retracted position.
Figure 5B:
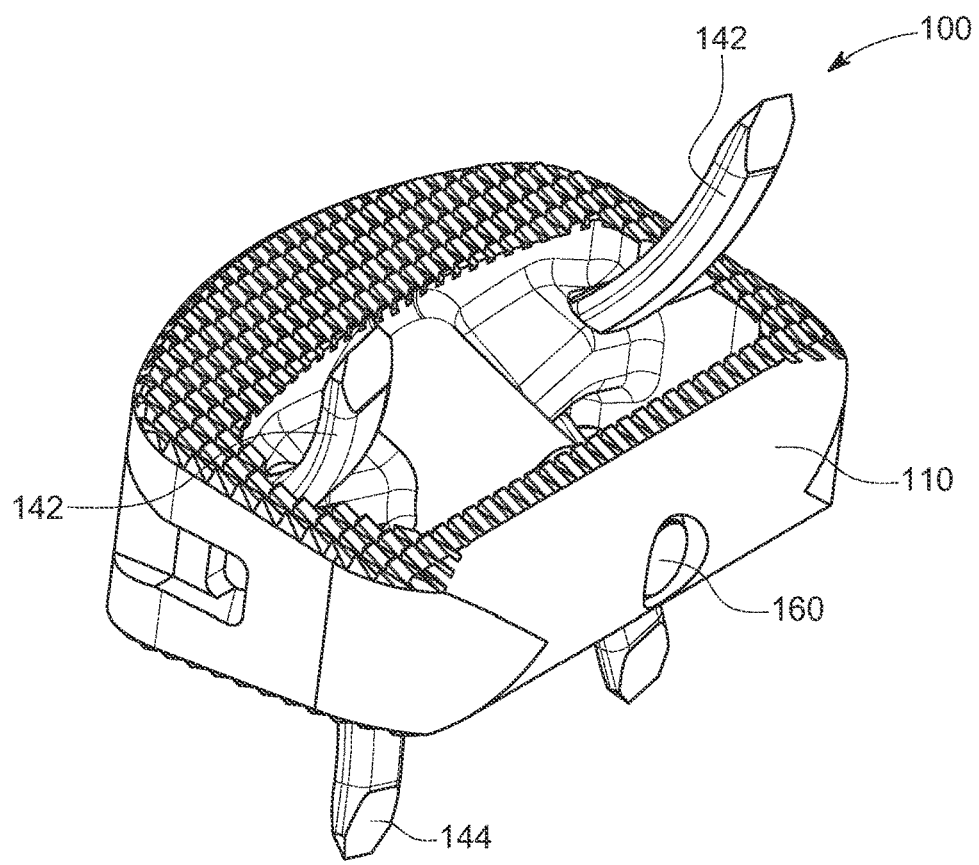
FIG. 5B illustrates a second isometric view of the lumbar vertebrae fusion device with internal extension mechanism in an extended position.

Referring to FIGS. 5A and 5B, a second isometric view of the lumbar vertebrae fusion device with internal extension mechanism in a retracted position and a second isometric view in an extended position are shown.

The rear view of the spinal stabilization device 100 shows the body 110 with upward protruding upper tangs 142 and downward protruding lower tangs 144.

The threaded actuator 160 is just visible after complete extension of the tangs 142/144.

Figure 6A:
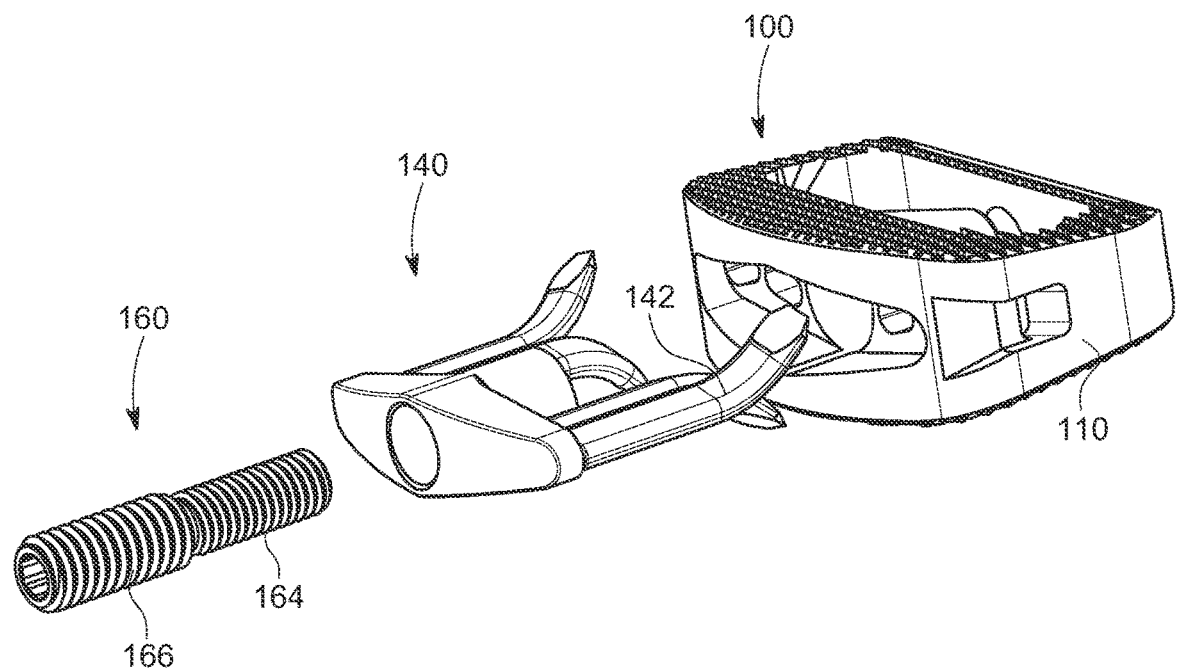
FIG. 6A illustrates an exploded view of the lumbar vertebrae fusion device with internal extension mechanism in a retracted position.
Figure 6B:
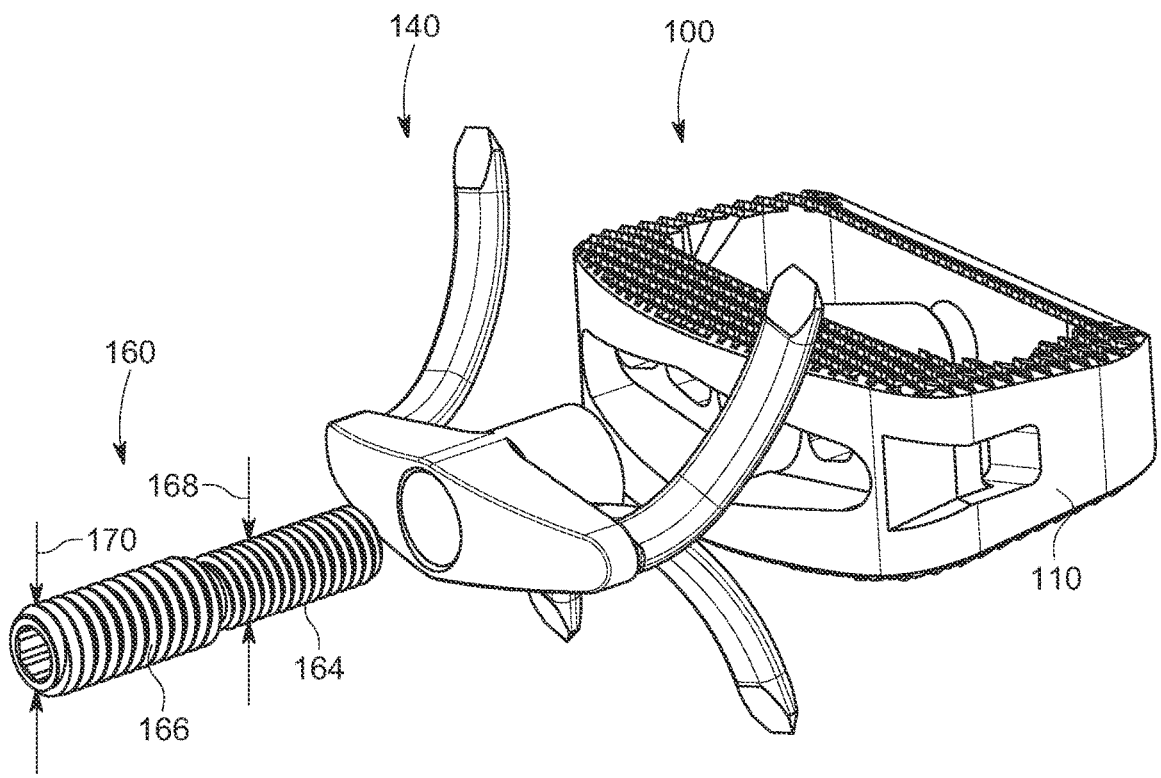
FIG. 6B illustrates an exploded view of the lumbar vertebrae fusion device with internal extension mechanism in an extended position.

Referring to FIGS. 6A and 6B, an exploded view of the lumbar vertebrae fusion device with internal extension mechanism in a retracted position and an exploded view in an extended position are shown.

The threaded actuator 160 is shown with first thread set 164, second thread set 166, first diameter 168, and second diameter 170.

The anchoring element 140 is visible before and after tang deformation.

Figure 7:
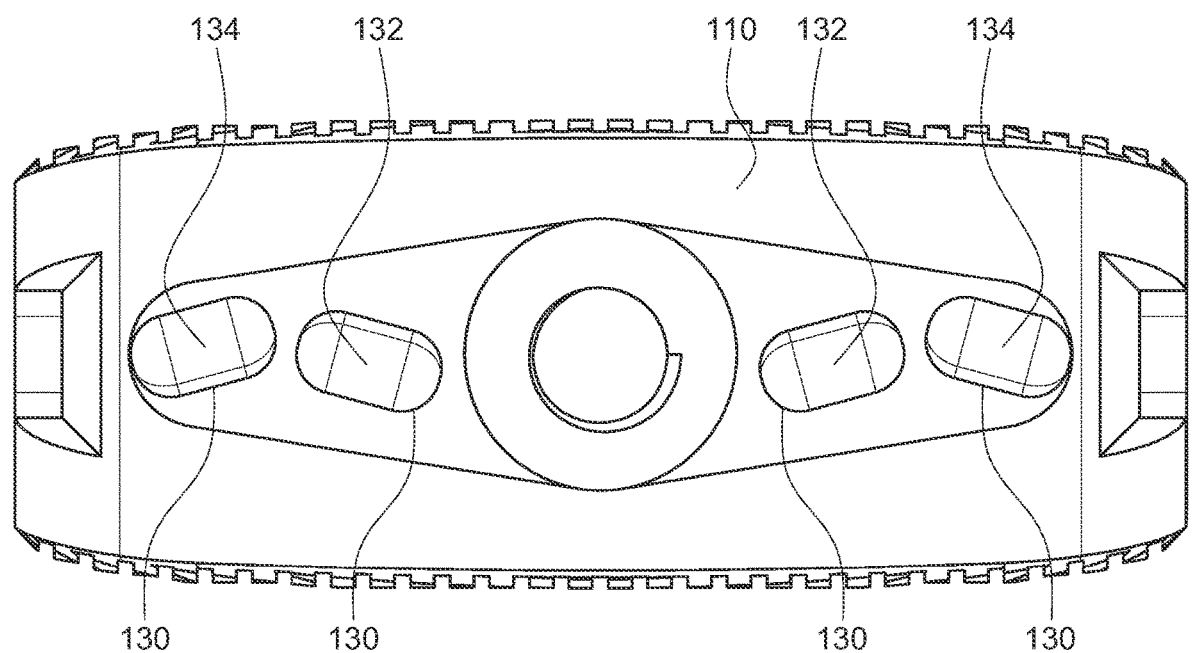
FIG. 7 Illustrates an end-on view of the body of the lumbar vertebrae fusion device with internal extension mechanism.

Referring to FIG. 7, an end-on view of the body of the lumbar vertebrae fusion device with internal extension mechanism is shown.

The body 110 includes a tang deflection passage 130 for each tang 142/144 (see FIG. 1B).

Each tang deflection passage 130 includes either a downward deflection ramp 132 or an upward deflection ramp 134 depending upon whether the associated tang 142/144 is to protrude through the top or the bottom of the body 110.

It is also noted that the tang deflection passages are angled outward to direct the tangs away from the center line of the body 110, widening their interface with the adjacent vertebrae to increase stability.

Figure 8:
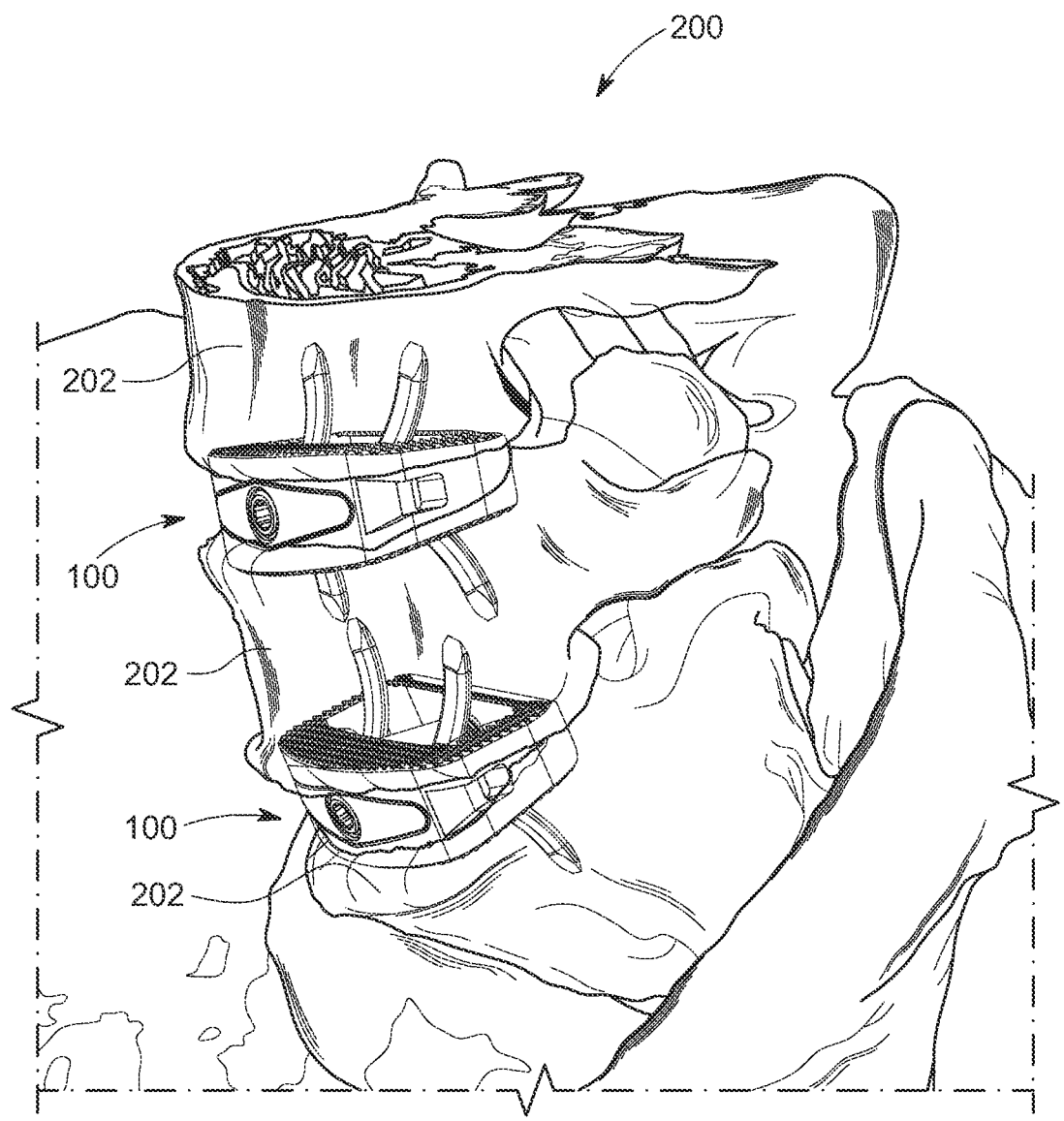
FIG. 8 illustrates an installed view of the lumbar vertebrae fusion device with internal extension mechanism.

Referring to FIG. 8, an installed view of the lumbar vertebrae fusion device with internal extension mechanism is shown.

Two spinal stabilization devices 100 are shown, each interfacing with two vertebrae 202 of the lumbar spine 200.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device for placement between a first vertebrae and a second vertebrae, the device comprising:
    a body;
    an anchoring element;
        one or more tangs joined to the anchoring element;
    a threaded actuator;
        rotation of the threaded actuator causing the anchoring element to move with respect to the body;
        movement of the anchoring element with respect to the body causing the one or more tangs to extend beyond the body;
    wherein the threaded actuator includes a first thread set and a second thread set;
        the first thread set interfacing with the body;
        the second thread set interfacing with the anchoring element;
        whereby user rotates the threaded actuator in a first direction to cause extension of the one or more tangs with respect to the body to join the device to the first vertebrae and the second vertebrae, or the user rotates the threaded actuator in a second direction to cause retraction of the one or more tangs with respect to the body to release the device with respect to the first vertebrae and the second vertebrae.

2. The device for placement between a first vertebrae and a second vertebrae of claim 1, wherein:
    the first thread set is a right hand thread and the second thread set is a left hand thread; or
    the first thread set is a left hand thread and the second thread set is a right hand thread.

3. The device for placement between a first vertebrae and a second vertebrae of claim 1, further comprising:
    one or more tang deflection passages;
        the one or more tang deflection passages integrated with the body;
        the one or more tangs of the anchoring element passing through the one or more tang deflection passages during movement of the anchoring element with respect to the body, the one or more tang deflection passages causing a change in shape of the one or more tangs.

4. The device for placement between a first vertebrae and a second vertebrae of claim 1, further comprising:
    a bone graft cavity within the body;
        the bone graft cavity for placement of bone graft material during insertion of the device to assist adjacent vertebrae with fusing through the body.

5. A device with integrated extendable tangs operated by an internal actuation mechanism, the device comprising:
    a body with an upper surface and a lower surface;
    an anchoring element;
        motion of the anchoring element causing motion of a set of upper tangs and a set of lower tangs;
        the anchoring element having a first position protruding from the body and a second position recessed into the body;
    a threaded actuator;
        rotation of the threaded actuator in a first direction causing the set of upper tangs and the set of lower tangs to move into the body;
        rotation of the threaded actuator in a second direction causing the set of upper tangs and the set of lower tangs to move out of the body;
    wherein the threaded actuator includes a first thread set and a second thread set;
        the first thread set interfacing with the body;
        the second thread set interfacing with the anchoring element;
        whereby rotation of the threaded actuator causes motion of the anchoring element with respect to the body;
    whereby a user places the device between a first and second vertebrae, rotating the threaded actuator in the first direction to cause extension of the set of upper tangs into a first vertebrae and to cause extension of the set of lower tangs into a second vertebrae.

6. The device with integrated extendable tangs operated by an internal actuation mechanism of claim 5, wherein:
    the first thread set is a right hand thread and the second thread set is a left hand thread; or
    the first thread set is a left hand thread and the second thread set is a right hand thread.

7. The device with integrated extendable tangs operated by an internal actuation mechanism of claim 5, further comprising:
    one or more tang deflection passages;
        the one or more tang deflection passages integrated with the body;
        the set of upper tangs and the set of lower tangs of the anchoring element pass through the one or more tang deflection passages during movement of the anchoring element with respect to the body, the one or more tang deflection passages causing a change in shape of the set of upper tangs and the set of lower tangs.

8. The device with integrated extendable tangs operated by an internal actuation mechanism of claim 5, further comprising:
    a bone graft cavity within the body;
        the bone graft cavity for placement of bone graft material during insertion of the device to assist adjacent vertebrae with fusing through the body.

9. A removable device to connect two adjacent vertebrae using extendable tangs, the device comprising:
    a body with an integrated tang actuation mechanism;
        the integrated tang actuation mechanism comprising:
            an anchoring element with an anchoring element head on a first end and upper tangs and lower tangs on a second end;
                the anchoring element having a first position where the upper tangs and the lower tangs are retracted into the body;
                the anchoring element having a second position where the upper tangs and the lower tangs are extended away from the body;

a threaded actuator;
the threaded actuator interfacing with the body via a first thread set;
the threaded actuator interfacing with the anchoring element via a second thread set;
the threaded actuator remaining within the body after implantation into a patient;
wherein the threaded actuator includes a first thread set and a second thread set;
the first thread set interfacing with the body;
the second thread set interfacing with the anchoring element;
whereby rotation of the threaded actuator causes motion of the anchoring element with respect to the body;
whereby a user rotates the threaded actuator to cause the anchoring element to move from the first position to the second position.

10. The removable device to connect two adjacent vertebrae using extendable tangs of claim 9, wherein:
the first thread set is a right hand thread and the second thread set is a left hand thread; or the first thread set is a left hand thread and the second thread set is a right hand thread.

11. The removable device to connect two adjacent vertebrae using extendable tangs of claim 9, further comprising:
one or more tang deflection passages;
the one or more tang deflection passages integrated with the body;
the upper tangs and the lower tangs of the anchoring element passing through the one or more tang deflection passages during movement of the anchoring element with respect to the body, the one or more tang deflection passages causing a change in shape of the upper tangs and the lower tangs.

12. The removable device to connect two adjacent vertebrae using extendable tangs of claim 9, further comprising:
a bone graft cavity within the body;
the bone graft cavity for placement of bone graft material during insertion of the device to assist adjacent vertebrae with fusing through the body.

* * * * *